United States Patent [19]
Jones

[11] Patent Number: 5,370,702
[45] Date of Patent: Dec. 6, 1994

[54] ACETABULAR CUP HAVING OPTIONALLY REMOVABLE PORTIONS

[75] Inventor: Scott A. Jones, Eighty Four, Pa.

[73] Assignee: Stelkast Incorporated, Pittsburgh, Pa.

[21] Appl. No.: 78,967

[22] Filed: Jun. 17, 1993

[51] Int. Cl.$^5$ .............................................. A61F 2/32
[52] U.S. Cl. ........................................ 623/22; 606/91; 606/92; 606/95
[58] Field of Search ...................... 623/16, 18, 19, 22, 623/23; 606/62, 91, 92, 95

[56] References Cited

U.S. PATENT DOCUMENTS

| | | | |
|---|---|---|---|
| 4,563,778 | 1/1986 | Roche et al. | 606/92 X |
| 4,566,138 | 1/1986 | Lewis et al. | 606/92 X |
| 4,955,325 | 9/1990 | Zarnowski et al. | 623/22 |
| 4,955,919 | 9/1990 | Pappas et al. | 623/22 |

*Primary Examiner*—Randall L. Green
*Assistant Examiner*—Mary Beth Jones
*Attorney, Agent, or Firm*—Kirkpatrick & Lockhart

[57] ABSTRACT

An acetabular cup having optionally removable portions to permit a choice between methods of affixation is provided. The cup has recesses in the surface of the wall of the cup. A post extends from the base of the recess inwardly toward the interior of the cup, but does not extend past the inner surface of the wall into the interior of the cup. A very thin annular section of the wall remains at the base of the recess. To open a hole, a tool is used to grasp and pull the post. The pulling force applied to the post causes the wall at the annular section to break or tear. The base and post is removed and a hole remains through which a fastener can be inserted. The hole or recess is configured to receive a standard bone screw, but may be configured to complement the shape of the head of any desired bone fastener.

10 Claims, 3 Drawing Sheets

ACETABULAR CUP HAVING OPTIONALLY REMOVABLE PORTIONS

BACKGROUND OF THE INVENTION

1. Field of the Invention

The present invention relates generally to acetabular cups. More specifically, it relates to an acetabular cup having optionally removable portions to permit a choice between methods of affixation.

2. Description of the Invention Background

Acetabular cups are used to replace the natural acetabulum, or hip socket, in instances of degenerative bone disease or severe fractures. Acetabular cups typically comprise a metallic cup which is fitted into a portion of the acetabulum which has been reamed to provide a mating fit with the cup. The inside of the metallic cup is fitted with a cup-shaped liner formed of ceramic or plastic, such as polyethylene. The femoral head (natural or prosthetic) fits into the cup-shaped liner. The metallic outer cup is presently held in place in the reamed natural acetabulum either by friction fit with or without cement, or by one or more screws.

Typically, a surgeon does not decide which method of affixation to use until the operation is underway. Only at this point can the surgeon directly observe the condition of the acetabulum to determine which method of affixation is desirable. In addition, if affixation by means of bone screws is adopted, one cannot determine in advance where the best place for insertion of a bone screw will be. Acetabular cups are, therefore, provided with a plurality of holes over the surface thereof for receiving bone screws if and where required. Metallic cups which are to be held in place by friction fit and cement, however, do not require holes. Even when screws are used to secure the cup to the natural bone, all of the holes provided in the metallic cups need not be used.

Experience has shown, however, that it is undesirable to implant a metallic cup with unused screw holes. The unused holes have been blamed for problems following surgery. Holes remaining in the wall of the cup allow debris to pass through and retard bone growth. The edges of the holes rub against the plastic liners to create plastic shavings. These shavings deteriorate the bone of the acetabulum. Also the shavings irritate the area where the bone is absorbed into the cup.

Zarnowski, U.S. Pat. No. 4,955,325, discloses an acetabular cup system capable of conversion from a cup constructed for affixation by fasteners to a cup suitable for cemented affixation. Zarnowski comprises a cup with a plurality of holes therein, spacers, and a spacer inserter for selectively inserting the spacers into the holes. The cup is designed with holes suitable for affixation with bone screws. The surgeon then has the option to decide after the operation is underway to use a cemented method of affixation. Using the spacer inserter tool, the user may snap spacers into the holes. The spacers project from the outer surface of the cup to maintain a gap for a layer of cement.

However, in Zarnowski, the spacers themselves have holes therein. Furthermore, the system disclosed in Zarnowski leaves extra holes in the cup when fewer screws are used to secure the cup to the natural bone than the number of holes provided in the cup. Additionally, the spacers are separate components, constituting multiple parts which must be stored.

There is a need for an acetabular cup which provides for the options between different methods of affixation and which eliminates unnecessary holes in the acetabular cup. There is a further need for an acetabular cup which does not include multiple components.

SUMMARY OF THE INVENTION

The present invention provides a single acetabular cup which can be affixed through either friction-fit affixation or through the use of fasteners. The invention provides a way for the surgeon implanting the cup to make a selection during the progress of the operation as to which method of affixation to use.

The present invention is an implant which includes a cup shaped member having an outer surface configured for replacement of an acetabulum and an inner surface defining opposing sides of a wall, and at least one optionally removable portion formed in the wall for defining a hole in the wall when the portion is removed. The optionally removable portion is preferably defined by a recessed area formed in the inner surface of the wall, and includes a base surrounded by a weakened perimeter and means, such as a post, extending from the base for transferring a force sufficient for separating the base from the wall along the perimeter to define a hole in the wall.

An advantage of the present invention is to provide an acetabular cup free of holes when the cup is affixed by a friction-fit method. Additionally, when the friction-fit method cannot be used, the surgeon, at his or her option, can create the number of holes actually necessary for affixation using fasteners by removal of one or more of the removable portions of the cup No unused holes remain.

The present invention thus provides an acetabular cup wherein debris is prevented from passing through the unused holes of the cup and thereby retarding bone growth.

The present invention thus further provides an acetabular cup wherein the metal of the cup and the fasteners do not rub the inner liner to form plastic shavings.

A further advantage of the present invention is that multiple parts are not required when a single cup allows selection between different methods of affixation.

BRIEF DESCRIPTION OF THE DRAWINGS

The present invention can be better understood by reference to the drawings wherein.

DETAILED DESCRIPTION OF THE PREFERRED EMBODIMENTS

Figure 1:
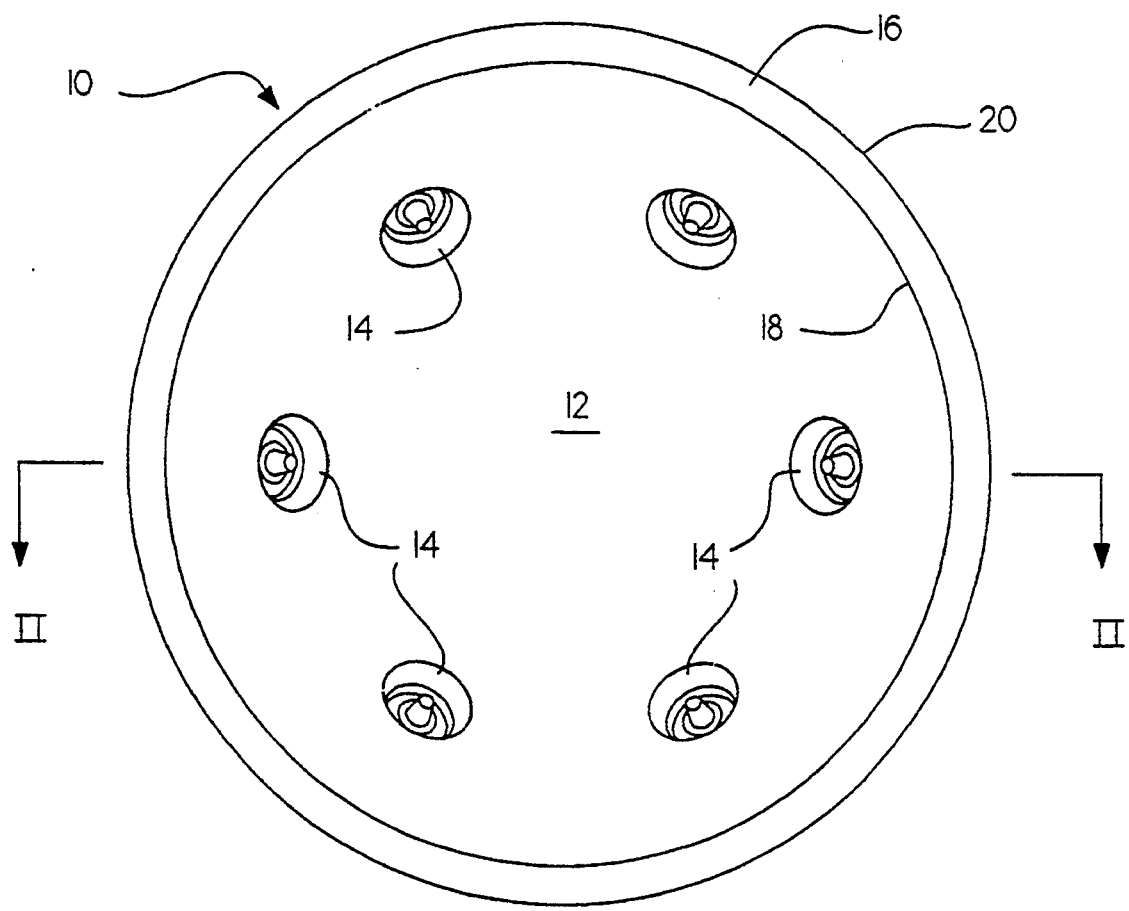
FIG. 1 is a bottom plan view of an acetabular cup showing a plurality of spaced optionally removable portions.
Figure 2:
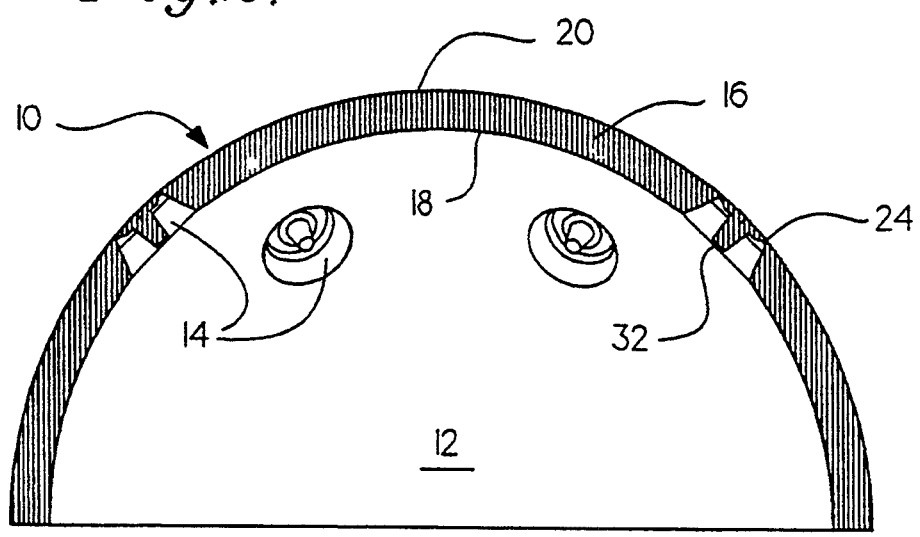
FIG. 2 is a side-sectional view of an acetabular cup taken along lines II—II of FIG. 1.

FIGS. 1–5 illustrate the preferred embodiments of the implant of the present invention. Referring to FIGS. 1 and 2, the acetabular cup 10 has a wall 16 with a generally concave inner surface 18 and a generally convex outer surface 20. Wall 16 has a generally uniform thickness X, preferably about 0.1 to 0.5 inches. Inner surface 18 is formed to receive a conventional cup-shaped plastic or ceramic liner (not shown). Outer surface 20 is formed for affixation into a natural acetabulum (not shown) which may be first reamed or otherwise prepared to receive cup 10. Outer surface 20 is shown to be substantially smooth, but may have any surface contour desired to best allow bone ingrowth to cup 10. The concave inner surface 18 of wall 16 defines interior portion 12 of cup 10.

Portions of wall 16 are removable, at the option of the surgeon, to define one or more holes through which fasteners can pass when the surgeon opts to use fasteners as the means for affixing the cup 10 to the natural bone. The optionally removable portions preferably take the form of areas of reduced thickness at the base of one or more recesses in wall 16. Other configurations of the removable portions may be provided in addition to or in place of the preferred configuration described herein. At least one removable portion, and preferably a plurality of removable portions, are provided. Recesses 14 are shown in the Figures as evenly spaced frustoconical recesses cut or formed in inner surface 18 of wall 16. In an alternative embodiment of the invention shown in FIG. 5, a second recess 14a can be formed on the outer surface 20 of wall 16. As described more fully below, each recess 14 must be configured to accept a bone screw or other fastener and to seat the head of the bone screw or fastener therein. Cup 10 can be made by manufacturing procedures known in the art, such as casting or machining. Recesses 14 can be machined by known techniques.

Figure 3:
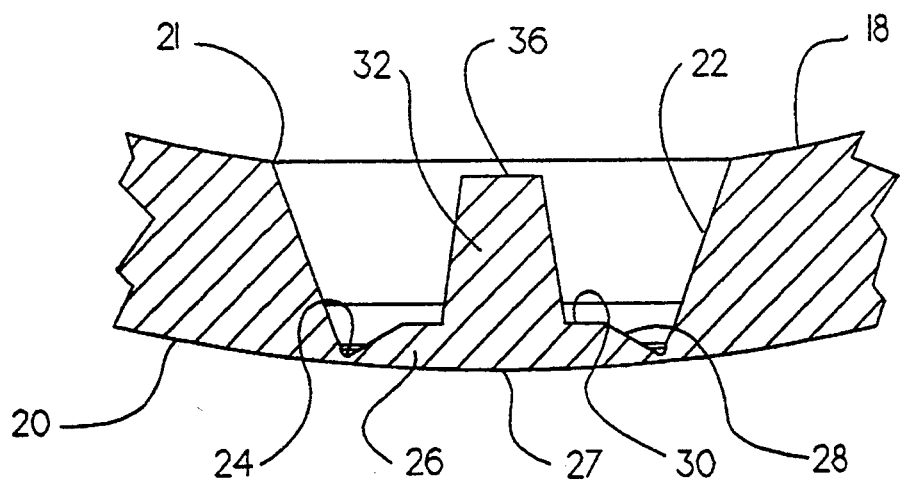
FIG. 3 is an enlarged fragmentary cross-sectional view of the optionally removable portion of the acetabular cup.
Figure 4:
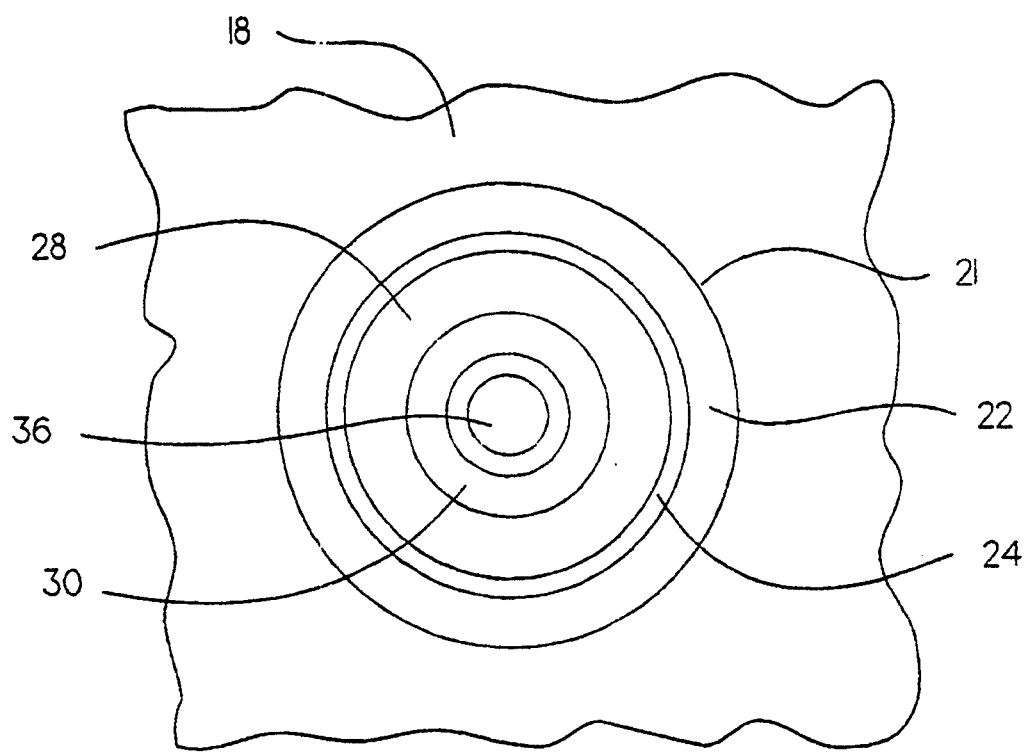
FIG. 4 is an enlarged plan view of the optionally removable portion of FIG. 3 as viewed from the interior of an acetabular cup; and, FIG. 5 is an enlarged fragmentary cross-sectional view of an alternative embodiment of the removable portion of an acetabular cup.

FIG. 3 shows an enlarged cross-section of a removable portion and FIG. 4 shows a top view of a removable portion from the interior of the cup 10. As shown in FIG. 3, a recess 14 formed in inner surface 18 of wall 16 has a frustoconical sidewall 22. The junction 21 between sidewall 22 and surface 18 is rounded to avoid a sharp edge. The rounded edge is preferable to prevent the plastic liner (not shown) from rubbing against the metal at a sharp edge and the consequent formation of plastic shavings. Recess 14 shown in the preferred embodiment is circular in shape, but other shaped recesses will work as well provided they are configured to receive a desired fastener. Similarly, sidewall 22 may be a shape other than frustoconical, again, depending on the configuration of the desired fastener.

Recess 14 has a base 26 having a raised shoulder 30 and a bevel 28 which slopes down to a thin, preferably annular, section 24 which defines the perimeter of the removable portion. Wall 16, base 26 and thin section 24 are preferably formed in one piece of the same material. For purposes of identification, however, the portion of outer surface 20 forming the outer surface of the base 26 in FIG. 3 is designated as outer face 27. The thickness X of wall 16 is significantly reduced at base 26 and even more so at thin section 24, such that the material of wall 16 at section 24 is weakened and can be easily broken or torn if a pulling and bending force is applied thereto. When a cup 10 having a wall 16 of 0.1 to 0.5 inches is used, then thin section 24 may, for example, be about 0.005 inches thick.

A member is provided to permit such a bending or breaking force to be transferred to the weakened perimeter at section 24. The member may be any configuration suitable for engagement with a tool. In the preferred embodiment of the invention, a post 32 is provided. Post 32 projects inwardly toward, but short of, interior portion 12 of cup 10. Post 32 is configured so that the thickness along its longitudinal axis from outer face 27 to top surface 36 is less than X so that it does not extend to or beyond inner surface 18. In this way, the plastic liner will not rub against post 32 when the removal portions are not removed. Post 32 is formed so that it can be grasped and held firmly with any suitable known tool (not shown) to exert the type and degree of force necessary and sufficient to tear or break weakened thin section 24. Other means for removing the base 26 can also be used. Post 32 may be replaced by a different configuration for applying a pulling and bending force to base 26. Similarly, the removable portion may be constructed so that a force other than a pulling or bending force—i.e., pushing, punching or twisting—may be applied to remove base 26 and form a hole in cup 10.

Figure 5:
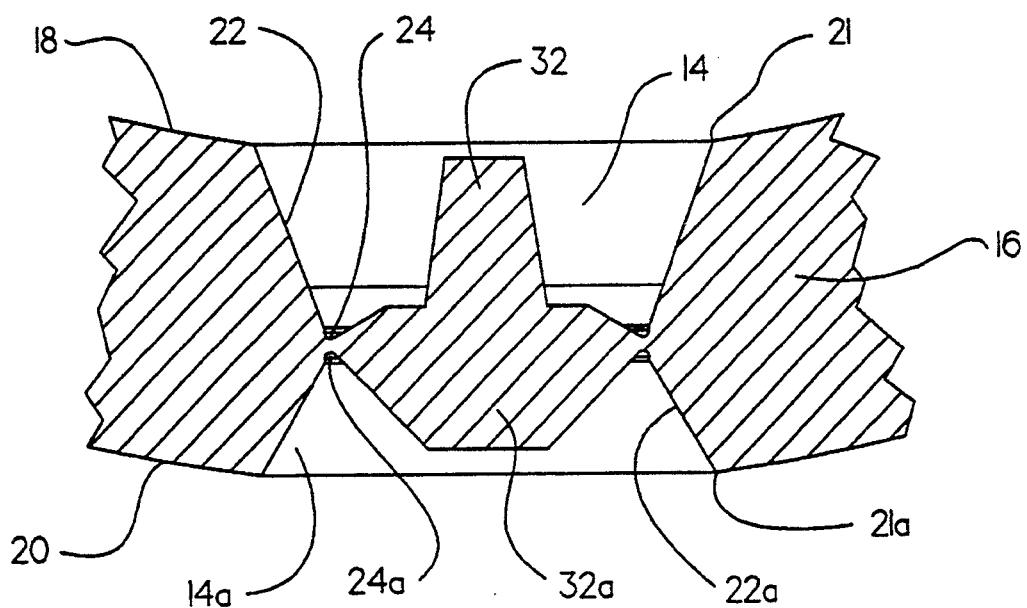

As shown in FIG. 5, one or more recesses 14a may also be formed on the outer surface 20 to permit the surgeon to remove the removable portions from either the interior or the exterior of the acetabular cup. Recess 14a may be formed in the same manner as recess 14, as shown. Other configurations are possible. Referring to FIG. 5, each recess 14a includes a post-like member 32a, a groove or thin section 24a, sidewall 22a and a junction 21a having smooth, rounded edges to avoid abrasion of the surface against which the cup ultimately rests. In yet another embodiment, the recess 14a may be just a groove or a groove and a shallow recess 14a opposite the thin section 24 and recess 14 of inner section 18 so that removal of the removable portion is easier.

A user desiring to affix cup 10 by means of bone screws or other fasteners can grasp post 32 (or post 32a) with a suitable grasping tool. By pulling on the tool the user will apply a force to base 26, which will create stress on inner thin section 24, and, if present, outer thin section 24a. The stress applied to thin sections 24, 24a will cause the material along the perimeter of the removable portion to break or to tear. The user can then remove base 26 and post 32 and discard them. This will leave a hole at the bottom of recess 14 (and recess 14a, if present) through which a fastener can pass. Recess 14 is pre-designed for receiving and seating the head of the bone screw or other fastener. The dimensions of the recess 14 are sufficient to permit the head of the bone screw or other fastener to be seated. Therefore, the head of the fastener will not rub the plastic liner and create plastic shavings which can interfere with bone growth. If sufficient for affixation purposes, only one removable portion needs to be removed. As many holes may be opened as, and where, necessary, with the advantage that no extra unused holes remain.

Alternatively, a user desiring to affix cup 10 by means of friction-fitting can simply use cup 10 without any alterations. Base outer face 27 is preferably flush with outer surface 20 and can be formed with the same desired surface pattern, if any, as outer surface 20 to provide an optimal surface for the bone to grow into. If this option is chosen, wall 16 of cup 10 has no holes through which debris can pass to retard bone growth. In embodiments of the invention having a recess 14a or thin section 24a on the outer surface 20 of the cup, the junction 21a where the outer wall surface meets the recess is smooth so abrasion of the natural bone surface or of cement will not be a problem.

It is to be understood that the above detailed description of a preferred embodiment of the invention is provided by way of example only. Various details of design and construction may be modified without departing from the true spirit and scope of the invention as set forth in the appended claims.

What is claimed is:

1. An implant comprising:
   a cup shaped member having a wall defined by an outer surface configured for replacement of an acetabulum and by an inner surface; and
   at least one removable portion defined by a weakened perimeter formed in said wall for defining a hole in said wall when said removable portion is removed.

2. The implant recited in claim 1 wherein said cup shaped member has a plurality of said removable portions.

3. An implant comprising;
   a cup shaped member having a wall defined by an outer surface configured for replacement of an acetabulum and by an inner surface; and
   at least one removable portion formed in said wall for defining a hole in said wall when said removable portion is removed wherein there are a plurality of said removable portions comprising: a plurality of spaced recessed areas formed in said wall, each recessed area having a base surrounded by a weakened perimeter and means extending from said base for transferring a force sufficient for separating said base from said wall along said perimeter to define a hole in said wall through said recessed area.

4. An implant comprising:
   a cup shaped member having a wall defined by an outer surface configured for replacement of an acetabulum and by an inner surface; and
   at least one removable portion formed in said wall for defining a hole in said wall when said removable portion is removed wherein said removable portion is defined by a weakened perimeter in said wall and includes means for transferring to said perimeter a force sufficient to separate said removable portion from said wall.

5. The implant recited in claim 4 wherein said means for transferring force is a member configured for engagement with a tool.

6. The implant recited in claim 5 wherein said member is a post.

7. An implant comprising:
   a cup shaped member having a wall defined by an outer surface configured for replacement of an acetabulum and by an inner surface; and
   at least one removable portion formed in said wall for defining a hole in said wall when said removable portion is removed wherein said wall has a first depth dimension and said removable portion has a perimeter defined by a second depth dimension, said second depth dimension being less than said first depth dimension and being sufficiently thin at said perimeter relative to said first depth dimension that said optionally removable portion separates from said wall at said perimeter upon the application of a breaking force sufficient to separate said removable portion from said wall.

8. The implant recited in claim 1 wherein said removable portion is formed in said inner surface of said cup shaped member.

9. The implant recited in claim 1 wherein said removable portion is formed in said outer surface of said cup shaped member.

10. An implant comprising:
    a cup shaped member having a wall defined by an outer surface configured for replacement of an acetabulum and by an inner surface; and
    at least one removable portion formed in said wall for defining a hole in said wall when said removable portion is removed wherein said removable portion is formed by opposing recessed areas in said inner and said outer surfaces, each recessed area having a base and a grooved perimeter therein sufficiently weakened to permit said base to be separated from said wall at said perimeter upon the application of a breaking force thereto.

* * * * *